United States Patent
Johnson et al.

(10) Patent No.: US 6,238,437 B1
(45) Date of Patent: *May 29, 2001

(54) ABLE-BODIED ARTIFICIAL FOOT PHOSTHESIS TESTING APPARATUS

(75) Inventors: Christopher L. Johnson, Plainwell; Eric L. Robinson, Sterling Heights, both of MI (US)

(73) Assignee: College Park Industries, Inc., Fraser, MI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/149,949

(22) Filed: Sep. 9, 1998

Related U.S. Application Data

(60) Provisional application No. 60/058,250, filed on Sep. 9, 1997.

(51) Int. Cl.[7] ........................................ A61F 2/74
(52) U.S. Cl. ........................ 623/27; 623/912; 623/53; 36/81; 36/136; 482/75
(58) Field of Search ............................. 623/27–29, 912, 623/53; 36/131–132, 81, 136; 74/594.4; 482/75

(56) References Cited

U.S. PATENT DOCUMENTS

| | | | | |
|---|---|---|---|---|
| 13,360 | * | 7/1855 | Rhodes | 623/28 |
| 433,365 | * | 7/1890 | Pitman | 623/28 |
| 3,070,807 | * | 1/1963 | Wheeler | 623/28 |
| 3,278,946 | * | 10/1966 | Godwin | 623/28 |
| 4,255,822 | * | 3/1981 | Dixon | 623/28 |
| 4,449,256 | * | 5/1984 | Prueitt | 623/28 |
| 5,150,903 | * | 9/1992 | Percic | 273/188 A |
| 5,593,373 | * | 1/1997 | Hale | 623/28 |
| 5,878,514 | * | 3/1999 | Ueda et al. | 36/131 |

FOREIGN PATENT DOCUMENTS

23199 * 3/1901 (GB) ........................................ 623/28

* cited by examiner

Primary Examiner—Bruce Snow
(74) Attorney, Agent, or Firm—Howard & Howard

(57) ABSTRACT

The present invention is footwear for use by an able-bodied person to test and appreciate the functions of a prosthetic foot. The footwear includes an upper for attachment to a user's foot and a mounting plate attached to the inside sole of the footwear. An adapter is mounted to the mounting plate for receipt of the foot prosthesis. The adapter allows for adjustment of the prosthesis with respect to the footwear.

14 Claims, 3 Drawing Sheets

ABLE-BODIED ARTIFICIAL FOOT PHOSTHESIS TESTING APPARATUS

This application claims a priority to U.S. provisional patent application Ser. No. 60/058,250, filed Sep. 9, 1997.

BACKGROUND

The present invention relates to an apparatus for allowing able-bodied individuals of varying sizes to test and appreciate the functions of a prosthetic foot during all walking phases, including the heel strike, mid-stance and toe off phases.

A problem with foot prosthesis is that someone with both feet cannot experience the foot's attributes. This is particularly problematic for prosthetists. A typical prosthetist cannot personally experience the foot functions of a foot prosthesis. The advantages and disadvantages of various foot prosthesis are only learned through communicating with the prosthesis manufacturer and the patient. Actually experiencing the foot's operation is not possible unless the prosthetist is an amputee.

SUMMARY OF THE INVENTION

The present invention overcomes the above problem by providing footwear to which a foot prosthesis can be attached and worn by an able-bodied individual. A person can then wear the footwear to experience the prosthetic. In the preferred embodiment, the footwear is a boot and more preferably an air cast boot. The boot has a mounting plate which is secured to the inside base of the boot. The mounting plate and the prosthesis have mating connectors for attaching the prosthesis to the boot. In the preferred embodiment, the mating connectors include an adapter that is fastened by screws to the mounting plate. The prosthesis has a mating member that is received by the adapter to fix the prosthesis to the adapter and mounting plate.

It should be appreciated by those of ordinary skill in the art that the preferred footwear is a boot, such as an air cast because it restrains movement of the wearer's foot and ankle. However, any type of footwear would work, such as for example a shoe, sandal, etc.

The foregoing detailed description shows that the preferred embodiments of the present invention are well suited to fulfill the objects of the invention. It is recognized that those skilled in the art may make various modifications or additions to the preferred embodiments chosen herein to illustrate the present invention, without departing from the spirit of the present invention. Accordingly, it is to be understood that the subject matter sought to be afforded protection should be deemed to extend to the subject matter defined in the appended claims, including all equivalents thereof.

DETAILED DESCRIPTION OF THE INVENTION

Figure 1:
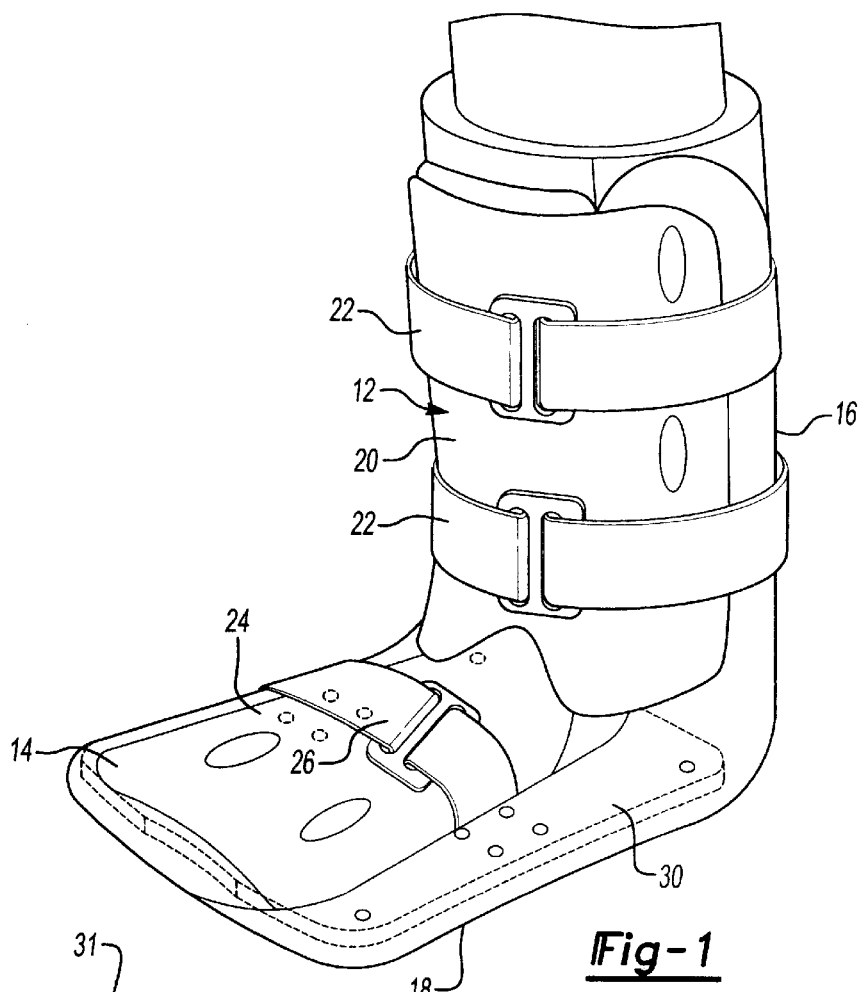
FIG. 1 is a perspective view of the preferred embodiment of the present invention.

In the preferred embodiment, the footwear 10, which is illustrated as an air cast, has an upper or calf support portion 12 and foot support portion 14. The back 16 of the calf support portion 12 and the sole dr base 18 of the foot support portion 14 are illustrated as an integrally formed unit to rigidly hold the leg with respect to the foot. A leg retention plate 20 can be secured to the front of the leg by straps 22 and a foot retention portion 24 can be strapped to the foot by straps 26. By tightening the straps, the user's leg and foot can be restrained within the air cast and the foot held rigid with respect to the leg. By inflating the bladders of the air cast through air tubes 21, the boot can be adjusted to fit different sizes and facilitate foot retention.

A mounting plate 30 shown in FIGS. 1–3 and 6 is mounted to the inside of the sole or base of the foot support portion 14. Fasteners 29, preferably cap screws with washers, are threaded through the base 18 of foot support portion 14 through openings 31 in the mounting plate 30. As shown in FIG. 1, the mounting plate 30 is on the inside of the boot. In the preferred embodiment, a foam pad is placed over the plate 30. The plate 30 is mounted to the inside of the boot to direct the individual's weight directly to the prosthetic 34 and not to the boot 10.

Figure 3:
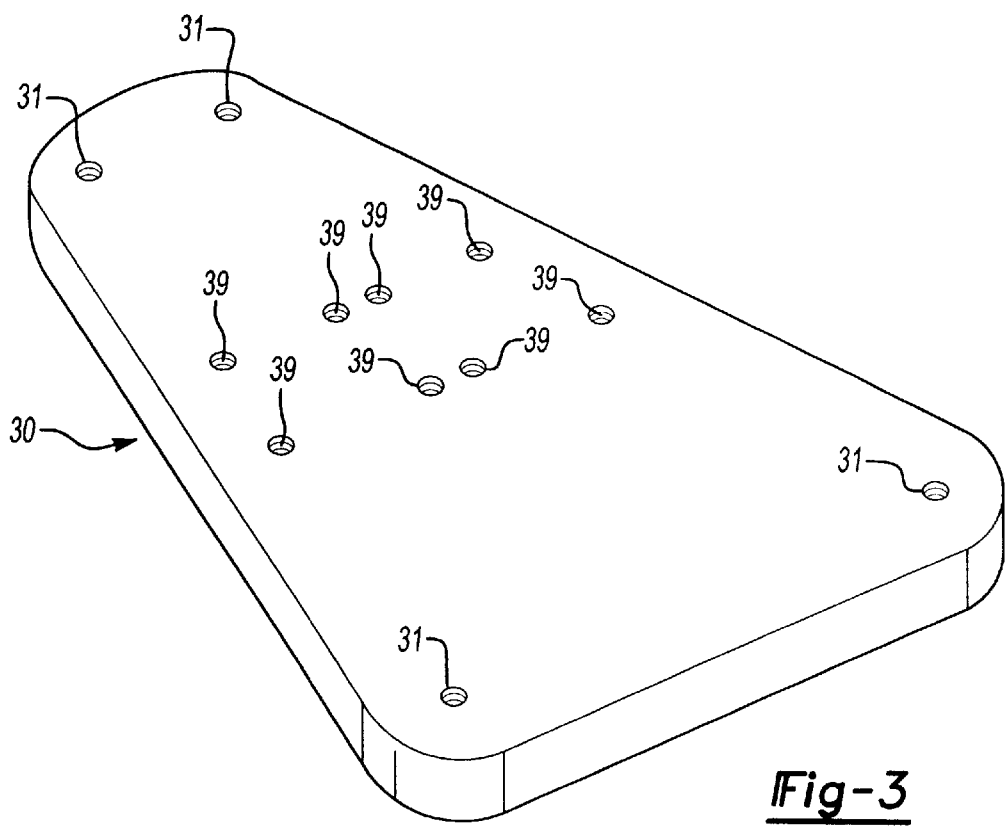
FIG. 3 is a perspective view of the mounting plate viewed from the top.

The illustrated mounting plate 30 is a preferred design, but it will be appreciated by those of ordinary skill in the art that other designs are available and would work for the intended purpose of mounting the prosthetic foot to the air cast. With reference to FIG. 3, the top of the mounting plate 30 is flat and is intended to form a surface on which foam padding is placed to comfortably support the user's foot. Preferably, bolt holes 31 are formed in the adapter plate to receive bolts, preferably cap screws 37 that are inserted through the base 14 of the air cast 10. It will be apparent to those of ordinary skill in the art that other methods of attaching the mounting plate 30 to the bottom of the foot portion 14 of the air cast are available and will provide adequate mounting means for mounting the plate to the air cast.

Figure 2:
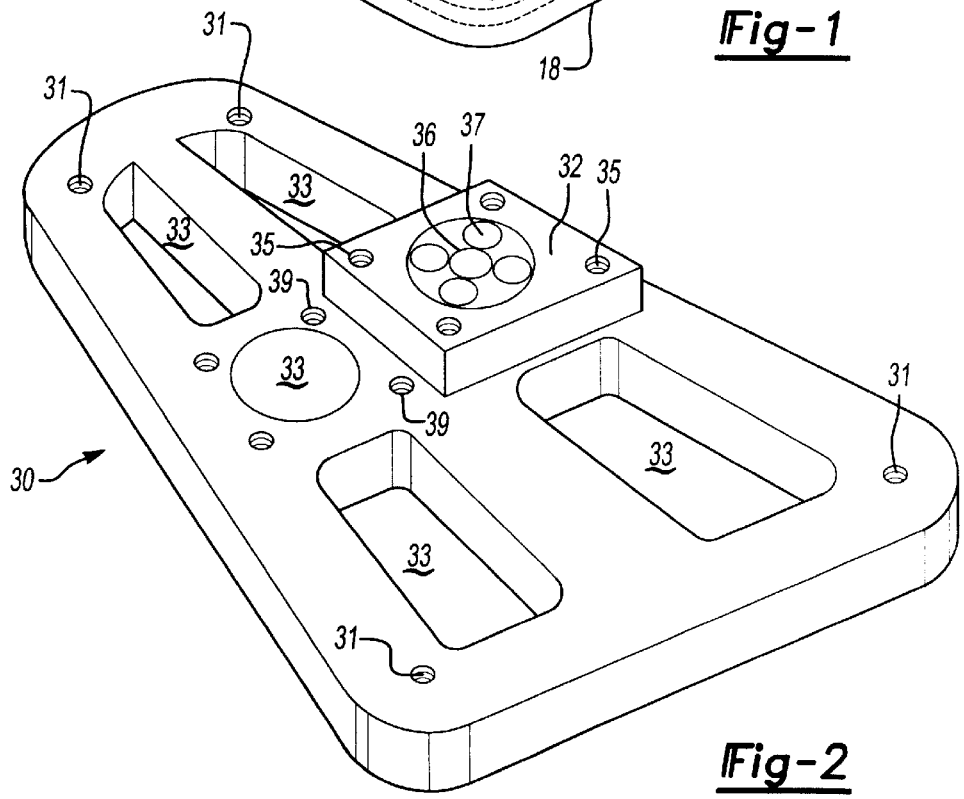
FIG. 2 is a perspective view of the mounting plate viewed from the bottom.

With reference to FIG. 2, the bottom of the mounting plate 30 is illustrated. The bottom has cut-outs 33 for weight reduction purposes. In the preferred embodiment, the mounting plate 30 is formed from an aluminum plate. The cut-outs 33 help to reduce the weight of the plate. It should be appreciated by those of ordinary skill in the art that materials other than aluminum can be used, such as for example plastic, steel, wood, etc. The material selected only needs to be sturdy enough to withstand the user's weight and to withstand the stress associated with walking on the attached prosthesis.

Figure 4:
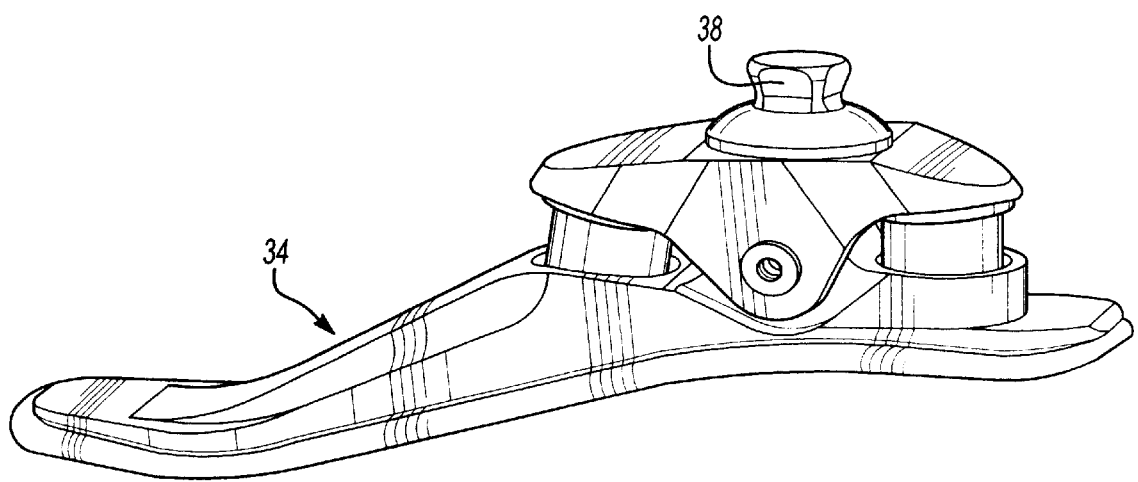
FIG. 4 is a perspective view of a prosthesis.
Figure 5:
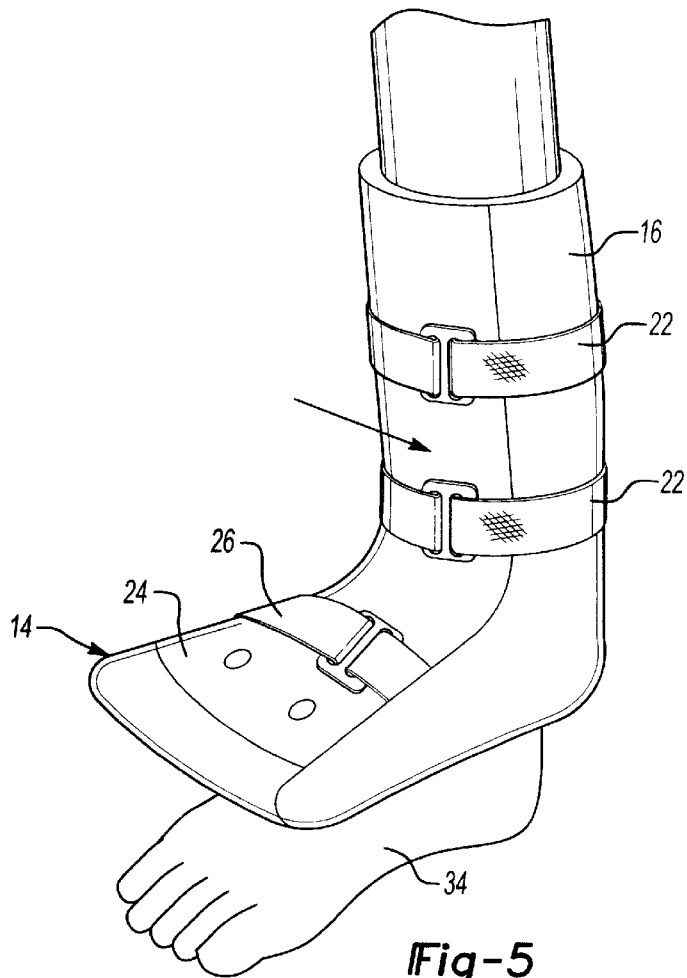
FIG. 5 is a perspective view of the preferred embodiment of the present invention with a foot prosthesis attached.
Figure 6:
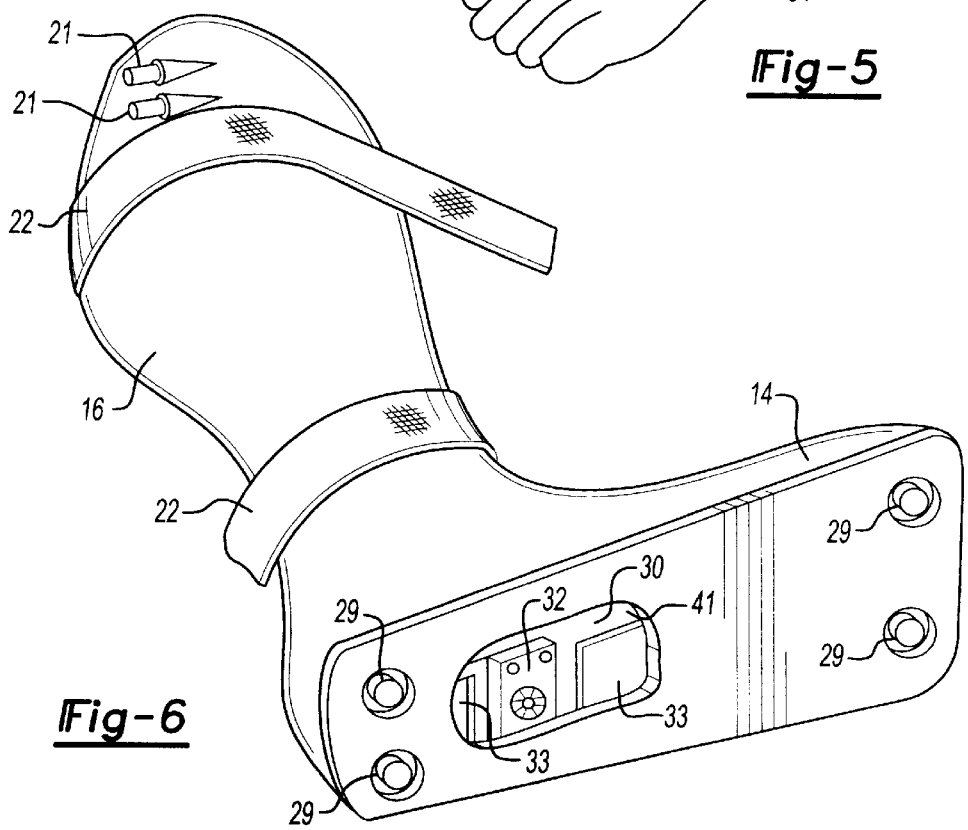
FIG. 6 is a prospective view from the bottom of the boot.

An adapter 32 is mounted to the mounting plate 30 for attaching the foot prosthesis 34 to the mounting plate 30 and the air cast. In the preferred embodiment, the adapter 32 is an Otlo Bock 4R51 Titanium Rotatable Adapter. The adapter 32 is shown bolted by bolts 35 to the mounting plate through bolt holes 39. Adapter 32 has a central recess at 36 which is configured to receive a pyramid 38 mounted to the top of the prosthesis 34. This can be seen in FIG. 4. As those of ordinary skill in the art will understand, pyramid 38 can be inserted into the recess 36 and then fixed by set screws that are threaded into openings 37. The bolts not only fix the pyramid, but also allow for adjustment. The adapter and pyramid allow adjustments for toe in and out, plantar flexion, dorsi flexion, inversion and eversion relative to the boot. The attached prosthesis is illustrated in FIG. 5. In FIG. 5, the prosthesis has a foot shaped cover over it.

To assemble the testing apparatus, an opening 41 is formed in the bottom of the boot 10. See FIG. 6. The mounting plate 30 is then inserted into the boot shell and cap screws 37 are threaded through the boot bottom and into threaded openings 31 in the plate 30. The adapter 32 is fixed to the plate 30 and is adjacent the opening 41. As shown in FIG. 2, there are two locations for the adapter, either left or right of the longitudinal centerline of the plate 30. The plate 30 is designed for left or right use and if left, the adapter must be left of center and if right, right of center to provide better balance.

Once the plate 30 is installed, the prosthesis pyramid 38 is inserted into adapter 32 and the set screws are installed to properly adjust the prosthesis with respect to the boot.

Once the foot is attached to the air cast and the user's leg and foot are secured within the air cast, the user can walk upon the foot prosthesis to experience the feel of the foot prosthesis through all walking phases including heel strike, mid-stance, and toe off. In the preferred embodiment, the user would wear an air cast with a prosthesis attached on each foot. If desired, the prosthesis could be different so that comparative testing can be done.

Other advantages and meritorious features of the present invention will become more fully understood from the following description of the preferred embodiments, the appended claims and the drawings, a brief description of which follows.

What is claimed is:

1. Footwear for use by able-bodied individuals to experience the effects of a foot prosthesis, said footwear comprising:
   a foot support portion adapted to receive a user's foot, the foot support portion having fasteners for fastening the foot support portion to the user's foot;
   a sole portion at a bottom of the foot support portion, the sole portion including a mounting plate that mates with the foot prosthesis for mounting the foot prosthesis to the foot support portion;
   said mounting plate includes a adapter repositionable between a left side of the mounting plate and a right side of the mounting plate for mounting the foot prosthesis to the footwear, said foot prosthesis having a mounting member, said adapter constructed to receive said mounting member;
   wherein an able-bodied user can fasten the foot support portion to the able-bodied user's foot and attach a foot prosthesis as the able-bodied user walks on the foot prosthesis.

2. The footwear of claim 1, wherein said foot support portion is a boot further including a calf support portion.

3. The footwear of claim 2, wherein said calf support portion includes a front plate adapted to engage the user's shin, said fasteners fastening the front plate to the calf support portion to entrap the user's calf within the calf support portion and further including a foot retention portion to engage a user's foot and thereby fix the user's foot and ankle from movement.

4. The footwear of claim 3, wherein said fasteners are adjustable straps, which engage the calf support portion and the front plate.

5. The footwear of claim 1, wherein said mounting plate includes connectors to connect the mounting plate to the sole portion of the footwear.

6. The footwear of claim 1, wherein the adapter is adjustable to facilitate the connection of the foot prosthesis to the sole portion and to permit adjustment of the prosthesis with respect to the foot support portion.

7. A mounting plate for use with footwear having a sole to permit an able bodied individual to experience the effects of a foot prosthesis of the type having a mounting pyramid, said adapter plate comprising:
   a first side adapted to be mounted to the inside of the footwear sole such that the adapter plate and the footwear are unitary;
   a second side opposite the footwear sole, wherein the second side includes an adapter with a recess adapted to receive a mounting pyramid on the foot prosthesis to allow the foot prosthesis to be mounted to the adapter plate;
   wherein the adapter plate is mounted to footwear and the foot prosthesis is mounted to the adapter plate to allow an able bodied user to wear the footwear and walk on the foot prosthesis to experience the effects of the foot prosthesis as the able bodied user walks on the foot prosthesis.

8. The mounting plate of claim 7, wherein the first side of the adapter plate is adapted for bolting to the inside of a footwear sole.

9. The mounting plate of claim 7, wherein the adapter includes adjusting screws adjacent the recess to allow adjustment of the foot prosthesis as it is installed to the adapter plate.

10. An apparatus for use by able bodied individuals to experience the effects of a foot prosthesis, said apparatus comprising:
    a foot prosthesis;
    a foot support portion adapted to receive a users foot, the foot support portion having fasteners for fastening the foot support portion to the users foot;
    a sole portion including an adapter to which the foot prosthesis is mounted, the adapter having set screws that mate with the foot prosthesis for mounting the foot prosthesis to the sole portion, the adapter includes a central recess, the foot prosthesis having a pyramid mounting member which mates with the central recess of the adapter;
    wherein an able bodied user can fasten the foot support portion to the able bodied user's foot then walk on the foot prosthesis to experience the effects of the foot prosthesis as the able bodied user walks on the foot prosthesis.

11. The apparatus of claim 10, wherein said foot support portion is a boot further including a calf support portion.

12. The apparatus of claim 11, wherein said calf support portion includes a front plate adapted to engage the user's shin, said fasteners fastening the front plate to the calf support portion to entrap the user's calf within the calf support portion and further including a foot retention portion to engage a user's foot and thereby fix the user's foot and ankle from movement.

13. The apparatus of claim 12, wherein said fasteners are adjustable straps, which engage the calf support portion and the front plate.

14. The apparatus of claim 10, wherein the mounting plate has first and second sides and at least one side has at least one cutout to reduce the overall weight of the mounting plate.

* * * * *